United States Patent
Raynal et al.

(10) Patent No.: US 12,364,960 B2
(45) Date of Patent: Jul. 22, 2025

(54) METHOD FOR OLIGOMERIZATION IN A REACTOR COMPRISING A GAS/LIQUID DOUBLE DISTRIBUTOR

(71) Applicant: IFP Energies nouvelles, Rueil-Malmaison (FR)

(72) Inventors: Ludovic Raynal, Rueil-Malmaison (FR); Alexandre Vonner, Rueil-Malmaison (FR); Pedro Maximiano Raimundo, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 170 days.

(21) Appl. No.: 18/269,044

(22) PCT Filed: Dec. 14, 2021

(86) PCT No.: PCT/EP2021/085590
§ 371 (c)(1),
(2) Date: Jun. 22, 2023

(87) PCT Pub. No.: WO2022/136013
PCT Pub. Date: Jun. 30, 2022

(65) Prior Publication Data
US 2024/0050911 A1 Feb. 15, 2024

(30) Foreign Application Priority Data
Dec. 23, 2020 (FR) ........................................ 2014021

(51) Int. Cl.
*B01J 10/00* (2006.01)
*B01J 4/00* (2006.01)
(Continued)

(52) U.S. Cl.
CPC ............. *B01J 10/002* (2013.01); *B01J 4/002* (2013.01); *B01J 19/26* (2013.01); *C07C 2/24* (2013.01)

(58) Field of Classification Search
CPC . B01J 10/002; B01J 4/002; B01J 19/26; B01J 4/004; B01J 2204/002;
(Continued)

(56) References Cited

U.S. PATENT DOCUMENTS

| 4,524,139 A | 6/1985 | Fuchs |
| 4,615,998 A | 10/1986 | Le Quan et al. |

(Continued)

FOREIGN PATENT DOCUMENTS

| CN | 110898698 A | 3/2020 |
| EP | 2318129 A1 | 5/2011 |
| WO | 2019011806 A1 | 1/2019 |

OTHER PUBLICATIONS

International search report PCT/EP2021/085590 dated Feb. 21, 2022 (pp. 1-2).

*Primary Examiner* — Ali Z Fadhel
(74) *Attorney, Agent, or Firm* — Csaba Henter; MILLEN, WHITE, ZELANO & BRANIGAN (57) ABSTRACT

The present invention relates to a gas/liquid reactor for the oligomerization of gaseous ethylene, comprising a gaseous ethylene injection device and a liquid injection device, said injection devices advantageously being arranged so that the injection of the liquid can bring about a reduction, by shear, of the size of the ethylene bubbles, during the injection of the gaseous ethylene. The gas/liquid reactor according to the present invention may be used for any gaseous olefinic feedstock injected into a liquid phase.

19 Claims, 6 Drawing Sheets

(51) Int. Cl.
*B01J 19/26* (2006.01)
*C07C 2/24* (2006.01)

(58) Field of Classification Search
CPC ....... B01J 2219/00103; B01J 2219/185; C07C 2/24; C07C 2/08; C07C 2/10; C07C 11/02; C07C 11/08; C07C 11/107
See application file for complete search history.

(56) References Cited

U.S. PATENT DOCUMENTS

| | | | |
|---|---|---|---|
| 5,845,993 A * | 12/1998 | Shirtum | B01F 23/23123 366/101 |
| 8,389,774 B2 * | 3/2013 | Becker | B01J 4/002 422/600 |
| 9,931,622 B2 | 4/2018 | Magna et al. | |
| 10,150,108 B2 | 12/2018 | Magna et al. | |
| 10,646,860 B2 | 5/2020 | Breuil et al. | |
| 11,207,657 B2 | 12/2021 | Augier et al. | |
| 2011/0137083 A1 * | 6/2011 | Pfeffinger | B01J 8/228 564/450 |
| 2013/0158321 A1 | 6/2013 | Olivier-Bourbigou et al. | |
| 2018/0009662 A1 | 1/2018 | Simanzhenkov et al. | |
| 2018/0318819 A1 | 11/2018 | Breuil et al. | |

* cited by examiner

METHOD FOR OLIGOMERIZATION IN A REACTOR COMPRISING A GAS/LIQUID DOUBLE DISTRIBUTOR

TECHNICAL FIELD

The present invention relates to the field of gas/liquid reactors for the oligomerization of olefins to linear olefins by homogeneous catalysis.

The invention also relates to the use of the gas/liquid reactor in a process for the oligomerization of a gaseous olefinic feedstock, preferably of gaseous ethylene, to give linear α-olefins such as 1-butene, 1-hexene or 1-octene, or a mixture of linear α-olefins.

PRIOR ART

The invention relates to the field of gas/liquid reactors, also known as bubble columns, and also to the use thereof in a process for the oligomerization of an olefinic feedstock, preferably of ethylene. One drawback encountered during the use of such reactors in ethylene oligomerization processes is the management of the gas headspace, corresponding to the upper part of the reactor in the gaseous state. Said gas headspace comprises gaseous compounds that are sparingly soluble in the liquid phase, compounds that are partially soluble in the liquid but which are inert, and also gaseous ethylene not dissolved in said liquid. The passage of gaseous ethylene from the liquid lower part of the reaction chamber to the gas headspace is a phenomenon referred to as breakthrough. In point of fact, the gas headspace is bled in order to remove said gaseous compounds. When the amount of gaseous ethylene present in the gas headspace is high, bleeding of the gas headspace leads to a not insignificant loss of ethylene, which is detrimental to the productivity and to the cost of the oligomerization process. Furthermore, a significant phenomenon of breakthrough means that a lot of gaseous ethylene has not been dissolved in the liquid phase and therefore has not been able to react, which is detrimental to the productivity and the selectivity of the oligomerization process.

In order to improve the efficiency of the oligomerization process notably in terms of productivity and of cost, it is thus essential to limit the phenomenon of breakthrough of the ethylene in order to improve its conversion in said process, while at the same time maintaining good selectivity for the desired linear α-olefins.

Figure 1:
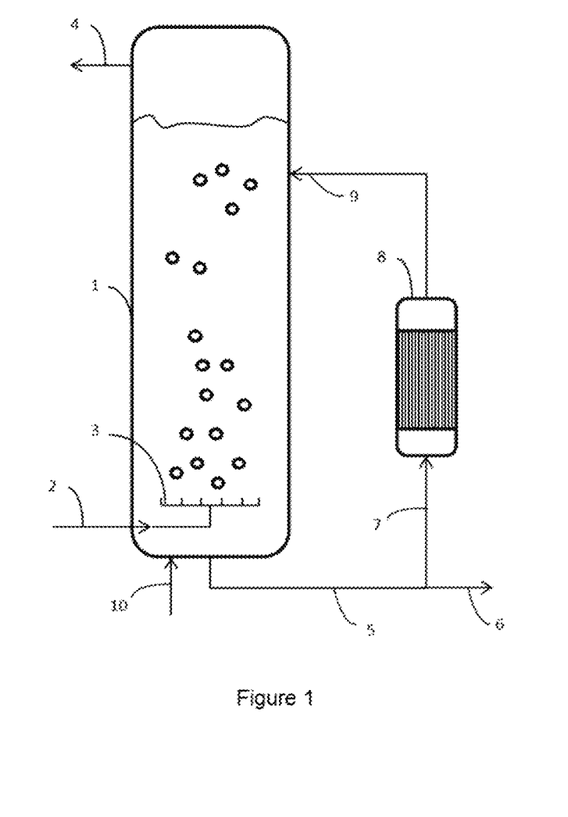

The prior art processes using a gas/liquid reactor, as illustrated in FIG. 1, do not make it possible to limit the loss of gaseous ethylene, and purging of the gas headspace results in an exit of gaseous ethylene from the reactor that is detrimental to the yield and the cost of the process.

In patent applications WO 2019/011806 and WO 2019/011609, the Applicant described processes enabling an increase in the contact surface area between the upper part of the liquid fraction and the gas headspace, by way of a dispersion means or vortex, so as to promote the passage of the ethylene contained in the gas headspace towards the liquid phase at the liquid/gas interface. These processes do not make it possible to limit the phenomenon of breakthrough and are insufficient when the amount of ethylene in the gas headspace is substantial because of a high level of breakthrough.

Moreover, during its research studies, the Applicant has found that, in a reactor operating with a constant flow rate of injected gaseous ethylene, the amount of dissolved ethylene and the phenomenon of breakthrough are dependent on the size of the bubbles of injected gaseous ethylene. The time devoted to the dissolution of the gaseous ethylene in the liquid phase corresponds to the time of travel of the bubbles in the liquid height, which is imposed by the operating conditions and the height of the reactor. The amount of gaseous ethylene dissolved per unit time is proportional to the area of contact between the gas and liquid phases. The larger the bubbles, the lower their area/volume ratio, and the longer the time required for dissolution, which increases the phenomenon of breakthrough for a given height of the liquid phase.

The Applicant has discovered that it is possible to improve the conversion of olefin(s), while at the same time maintaining high selectivity towards the desired linear olefin (s), and notably towards α-olefin(s), by limiting the phenomenon of breakthrough by means of a particular gas/liquid reactor for the oligomerization of a gaseous olefinic feedstock, in particular of gaseous ethylene, comprising a gaseous ethylene injection device and a liquid injection device, said injection devices advantageously being arranged so that the injection of the liquid can bring about a reduction in the ethylene bubble size, by shear, during the injection of the gaseous ethylene. The gas/liquid reactor according to the present invention may be used for any gaseous olefinic feedstock injected into a liquid phase.

BRIEF DESCRIPTION OF THE INVENTION

The present invention relates to a gas/liquid reactor for the oligomerization of a gaseous olefinic feedstock, comprising a gas injection device (3) and a liquid injection device (12), said injection devices being arranged so that the injection of the liquid can bring about a reduction, by shear, of the bubble size during the injection of the gaseous olefinic feedstock.

Preferably, the gas injection device (3) comprises at least one gas injection orifice and the liquid injection device (12) comprises at least one liquid injection orifice, each gas injection orifice being located close to an orifice of the liquid injection device (11) and positioned so that the injection trajectory of the gas is in the plane of the injection trajectory of the liquid.

Preferably, the liquid injection orifices and the gas injection orifices are circular, and the liquid injection orifices have a diameter greater than or equal to the diameter of the gas injection orifices.

Preferably, at least one gas injection orifice and at least one liquid injection orifice are positioned facing each other at an angle of between 0° and 180°.

Preferably, the gas injection and liquid injection devices are chosen from a pipe, a network of pipes, a multitubular distributor, a perforated plate, a cylindrical tube and a concentric tube.

Preferably, the gas injection device is a cylindrical tube in the form of a circular ring having injection orifices and the liquid injection device is a cylindrical tube in the form of a circular ring having injection orifices.

Preferably, the gas injection device in the form of a circular ring has a diameter less than that of the liquid injection device in the form of a circular ring, and said gas injection device is positioned inside the liquid injection device on a different plane.

Preferably, a sequence of several liquid and gas injection devices in the form of a circular ring of decreasing diameters are alternated from the periphery to the centre represented by the central axis of the device having the largest diameter, said devices being positioned so that a gas injection orifice of a gas injection device is positioned close to an orifice of the adjacent liquid injection device so that the injection trajectory of the liquid is in the same plane as the injection trajectory of the gas so as to bring about shear of said gas.

Preferably, the orifices of the gas and liquid injection devices are each extended by a tube (13, 15).

Preferably, the tube(s) (13) of the gas injection device (3) have a diameter smaller than that of the tube(s) (15) of the liquid injection device (12) and the open outlet end of the tube (13) of the gas injection device (3) is positioned coaxially inside the liquid injection tube.

Preferably, the liquid injection tube (15) comprises a deflector.

Preferably, the end of the liquid injection tube (15) has tapering of the outlet diameter.

Preferably, the reactor also comprises
a reaction chamber, of elongated shape along a vertical axis, which may contain
a liquid phase located in a lower zone, comprising and preferably consisting of the products of the reaction, dissolved and gaseous olefinic feedstock, preferably dissolved and gaseous ethylene, a catalytic system and an optional solvent, and a gas phase, located in an upper zone above the lower zone, comprising gaseous olefinic feedstock, preferably gaseous ethylene, and also uncondensable gases (notably ethane),
a means for introducing the catalytic system, said means being located in the lower part of the reaction chamber,
a recirculation loop comprising a withdrawing means at the base (preferably at the bottom) of the reaction chamber for withdrawing a liquid fraction, a heat exchanger enabling the cooling of said liquid, and a means for introducing said cooled liquid, said introduction means being located in the upper part of the lower zone of the reaction chamber,
and optionally a gas phase recycling loop to recycle at least a fraction of the gas phase into the lower zone of the liquid phase, comprising a withdrawing means located in the upper zone of the reaction chamber to enable the withdrawal of a gas fraction in the gas phase and an introduction means positioned in the lower zone of the reaction chamber to enable the introduction of said withdrawn gas fraction into the liquid phase.

Another subject of the present invention relates to a process for the oligomerization of a gaseous olefinic feedstock using a gas/liquid reactor as defined previously, said process comprising the contact of a liquid comprising a catalytic system comprising a metal catalyst, at least one activator and at least one additive, and optionally a solvent, and gaseous olefinic feedstock by means of a gas injection device and a liquid injection device, said injection devices being arranged so that the injection of the liquid brings about a reduction, by shear, of the size of the gaseous ethylene bubbles.

Preferably, the gaseous olefinic feedstock comprises between 2 and 6 carbon atoms, preferably between 2 and 4 carbon atoms.

Preferably, the injection speed of the liquid is greater than the injection speed of the gaseous olefinic feedstock so as to promote shear of the size of the olefin gas bubbles to gas bubbles of smaller size.

Definitions & Abbreviations

Throughout the description, the terms or abbreviations below have the following meaning.

The term "oligomerization" means any addition reaction of a first olefin to a second olefin, which may be identical to or different from the first olefin. The olefin thus obtained has the empirical formula $C_nH_{2n}$, where n is equal to or greater than 4.

The term "linear α-olefin" means an olefin on which the double bond is located at the terminal position of the linear alkyl chain.

The term "catalytic system" means a chemical species which enables the use of the catalyst. The catalytic system may be a metal precursor comprising one or more metal atoms or a mixture of compounds for catalysing a chemical reaction, and more specifically an olefin oligomerization reaction. The mixture of compounds comprises at least one metal precursor. The mixture of compounds may also comprise an activator. The mixture of compounds may comprise an additive. The compound or the mixture of compounds may optionally be in the presence of a solvent.

The term "liquid phase" means the mixture of all of the compounds which are in a liquid physical state under the temperature and pressure conditions of the reaction chamber.

The term "gas phase" means the mixture of all of the compounds which are in the gaseous physical state under the temperature and pressure conditions of the reaction chamber: in the form of bubbles present in the liquid, and also in the top part of the reactor (gas headspace of the reactor).

The term "lower zone of the reaction chamber" means the part of the chamber that comprises the liquid phase, the gaseous olefinic feedstock, in particular gaseous ethylene, advantageously in the form of bubbles or dissolved, products of the reaction such as the desired linear α-olefin (i.e. 1-butene, 1-hexene, 1-octene or the mixture of linear α-olefins), the catalytic system and optionally a solvent. Preferably, the lower zone of the reaction chamber represents at least half and preferably three-quarters of the total volume of the reaction chamber.

The term "upper zone of the reaction chamber" means the part of the chamber that is located at the apex of the chamber, i.e. directly above the lower zone and consisting of the gas phase corresponding to the gas headspace.

The term "uncondensable gas" means a species in gaseous physical form which only partially dissolves in the liquid under the temperature and pressure conditions of the reaction chamber and which can, under certain conditions, accumulate in the headspace of the reactor (for example here: ethane).

The terms "reactor" or "device" denote all of the means enabling the implementation of the oligomerization process according to the invention, notably such as the reaction chamber and the recirculation loop.

The term "lower part of the reaction chamber" means the lower quarter of the reaction chamber, in the lower zone containing the liquid phase.

The term "upper part of the reaction chamber" means the upper quarter of the reaction chamber and belonging to the lower zone which is intended to contain the liquid phase.

The expression "degree of saturation with dissolved gaseous olefinic feedstock, in particular dissolved ethylene" denotes the ratio of the amount of dissolved gaseous olefinic feedstock, in particular of dissolved ethylene, to the maximum amount of the dissolved gaseous olefinic feedstock, in particular of ethylene, which it is possible to dissolve in the liquid under the temperature and pressure conditions considered.

The various components of the reactor will be described with reference to all of the figures, each component retaining the same reference sign from one figure to another.

BRIEF DESCRIPTION OF THE FIGURES

FIG. 1 illustrates a reactor according to the prior art. This reactor consists of a reaction chamber 1 comprising a lower zone comprising a liquid phase and an upper zone comprising a gas phase, a means for introducing the gaseous olefinic feedstock 2, in particular gaseous ethylene, via a gas injection device 3, into the liquid phase. The gas phase in the upper part of the reaction chamber 1 comprises a bleed means 4. A pipe for the withdrawal of a liquid fraction 5 is located in the bottom of the reaction chamber 1. Said fraction 5 is divided into two streams, a first, main stream 7 which is sent to a heat exchanger 8 and then introduced via a pipe 9 into the liquid phase, and a second stream 6, which corresponds to the effluent sent to a later step. The pipe 10 in the bottom of the reaction chamber enables the introduction of the catalytic system.

FIG. 2 represents a reactor according to the invention. This reactor differs from that of FIG. 1 in that the stream exiting the heat exchanger 8 is divided into two streams 9 and 11, and the stream 11 is sent into the liquid zone of the same chamber 1 via a liquid injection device 12 arranged with the gas injection device 3 so that the injection of the liquid can bring about, by shear, a reduction in the size of the ethylene bubbles during the introduction of the gaseous ethylene and of the stream 11.

In FIG. 3B, the liquid device 12 is on a plane below that of the gas injection device 3, such that the orifices of the gas injection device 3 are positioned on the trajectory of the orifices 14 of the liquid injection device 12.

DETAILED DESCRIPTION OF THE INVENTION

It is specified that, throughout this description, the expression "between . . . and . . . " should be understood as including the limits mentioned.

Within the meaning of the present invention, the different embodiments presented can be used alone or in combination with each other, without any limit to the combinations.

For the purposes of the present invention, the various ranges of parameters for a given step, such as the pressure ranges and the temperature ranges, may be used alone or in combination. For example, for the purposes of the present invention, a preferred range of pressure values can be combined with a more preferred range of temperature values.

Throughout the description and in the claims, the positions ("bottom", "top", "above", "below", "horizontal", "vertical", "lower half", etc.) of the various elements are defined relative to the column in the operating position.

The present invention relates to a gas/liquid reactor for the oligomerization of a gaseous olefinic feedstock, comprising a gas injection device and a liquid injection device, said injection devices being arranged so that the injection of the liquid can bring about a reduction, by shear, of the bubble size of the gaseous olefinic feedstock during the injection of said feedstock.

For the purposes of the present invention, the gas injection device is intended to inject an olefinic feedstock in gaseous form into an oligomerization reactor.

Advantageously, the reactor according to the invention makes it possible to improve the dissolution of the gaseous olefins in the liquid phase which contains the catalytic system and to reduce the speed of ascent of the gaseous olefins in the liquid phase, which synergistically reduces the phenomenon of breakthrough. Specifically, the smaller the injected gaseous olefin bubbles, the lower their speed of ascent in the liquid phase.

Thus, advantageously, the degree of saturation with dissolved gaseous olefins, preferably with dissolved gaseous ethylene, in the liquid phase is greater than 70.0%, preferably between 70.0% and 100%, preferably between 80.0% and 100%, preferably between 80.0% and 99.0%, preferably between 85.0% and 99.0% and even more preferably between 90.0% and 98.0%.

The degree of saturation with dissolved gaseous olefins, preferably with dissolved gaseous ethylene, can be measured by any method known to those skilled in the art, for example by gas chromatography (commonly referred to as GC) analysis of a fraction of the liquid phase withdrawn from the reaction chamber.

Another advantage of the present invention is that it improves the conversion of the olefinic feedstock, in particular of ethylene, and/or the selectivity for olefins, in particular α-olefins, and also the volumetric productivity of the oligomerization process.

Thus, another advantage of the reactor according to the invention is that it makes it possible to reduce the reaction volume and thus the dimensions of the reactor for identical performance relative to a reactor according to the prior art.

Reactor

The present invention relates to a gas/liquid reactor for the oligomerization of a gaseous olefinic feedstock, comprising a gas injection device and a liquid injection device, said injection devices being arranged so that the injection of the liquid can bring about a reduction, by shear, of the bubble size during the injection of the gaseous olefinic feedstock.

The effect of shear of the gas stream by the liquid stream makes it possible to break down the gas bubbles, and hence to reduce their size and thus improve their dissolution in the liquid phase. Thus, the arrangement of the gas and liquid injection devices according to the invention makes it possible to reduce the size of the gas bubbles, preferably of gaseous ethylene, to accelerate the dissolution of the gas, preferably of gaseous ethylene, in the liquid phase.

Preferably, the gas/liquid oligomerization reactor is a gas/liquid reactor for the dimerization, trimerization or tetramerization of ethylene.

The gas injection device 3 comprises at least one gas injection orifice and the liquid injection device 12 at least one liquid injection orifice, each gas injection orifice being located close to an orifice of the liquid injection device 11 and positioned so that the injection trajectory of the gas is in the plane of the injection trajectory of the liquid. The injection of the liquid can then bring about the shear of the injected gas and result in a decrease in the size of the gas bubbles, making it possible to improve the dissolution of the gas in the liquid phase by increasing the interface between the gas and the liquid.

It is understood that, for the purposes of the present invention, the gas and liquid injection devices may comprise a plurality of orifices for the injection of gas and of liquid, respectively, as a function of the dimensions of the reactor.

Advantageously, the reactor according to the invention, with the particular arrangement of the gas and liquid injection devices, makes it possible to reduce the size of the injected gas bubbles by at least 20% relative to the size of the injected gas bubbles without shear. Preferably, the percentage decrease in the size of the gas bubbles by shear is at least 25% relative to the size of the injected gas bubbles without shear, preferably at least 30%, preferably at least 35% and in a preferred manner at least 40%.

Advantageously, the breakdown of a gas bubble into two smaller bubbles of the same size gives rise to a 26% increase in the area of exchange between the gas and the liquid, the breakdown of a gas bubble into four smaller bubbles of the same size gives rise to a 59% increase, and the breakdown of a gas bubble into six smaller bubbles of the same size gives rise to an 82% increase. Hence, a reactor according to the invention facilitates and thus significantly improves the absorption of gas in the liquid phase, which makes it possible to increase the saturation with gaseous olefins in the liquid phase and to limit the phenomenon of breakthrough.

Preferably, the gas injection device 3 is chosen from a pipe, a network of pipes, a multitubular distributor, a perforated plate, a cylindrical tube, a concentric tube or any other means known to a person skilled in the art.

The term "injection orifice" means a round hole, an oval hole, a slit or any other form for injecting the liquid or the gas into the reactor.

Preferably, the gas injection orifices are circular, i.e. round holes. Preferably, the gas injection orifices have a diameter of between 1.0 and 20.0 mm, preferably between 3.0 and 15.0 mm, in order to form ethylene bubbles of millimetric size in the liquid.

Preferably, the liquid injection orifices have a diameter of between 1.0 and 15.0 mm, preferably between 3.0 and 20.0 mm.

Preferably, the liquid injection orifices are circular, i.e. round holes. Preferably, the gas and liquid injection orifices are circular and the liquid injection orifices have a diameter greater than or equal to the diameter of the gas injection orifices. Preferably, the ratio between the diameter of a gas injection orifice and the diameter of the liquid injection orifice arranged close to said gas injection orifice is between 0.1 and 1.0, preferably between 0.4 and 0.8.

In a preferred embodiment, the orifices of the gas and/or liquid injection devices are extended by a tube. Preferably, the orifices of the gas and liquid injection devices are extended by a tube and the gas injection tubes 13 of the gas injection device have a diameter smaller than that of the tubes of the liquid injection device 15, the open outlet end of each gas injection tube 13 preferably being positioned coaxially inside a liquid injection tube. The outlet orifice of the gas injection tube is directed towards the outlet orifice of the liquid injection tube.

Figure 5A:
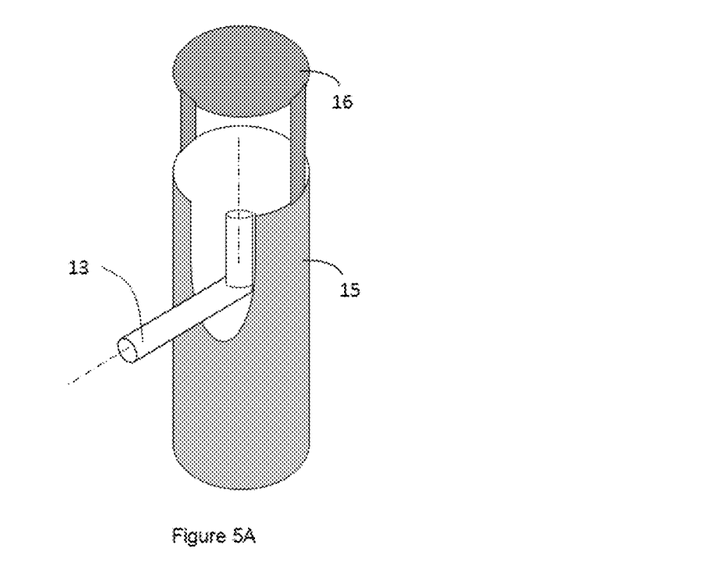
FIG. 5A illustrates a variant of the embodiment of FIG. 4 consisting in positioning a deflector 16 at the end of the liquid injection tube 15. Obstruction of the gas-liquid flow at the outlet of the device entrained by the deflector makes it possible to improve the shear of the gas bubbles by generating additional turbulence which makes it possible to improve the breakdown of the gas bubbles into gas bubbles of smaller size.

Preferably, the liquid injection tube 15 comprises a deflector as a means for partial closure of the tube, preferably a circular or square plate, which may or may not be perforated, as illustrated in FIG. 5A. Advantageously, the deflector makes it possible to improve the effect of shear of the gas bubbles by the liquid.

Figure 5B:
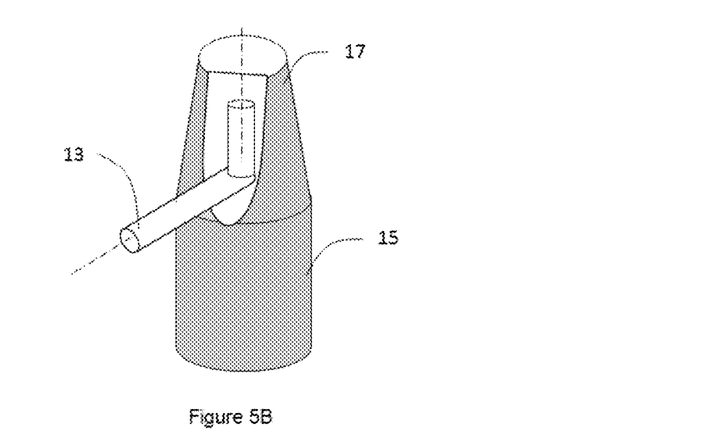
FIG. 5B illustrates a variant of the embodiment of FIG. 4 consisting of tapering 17 at the end of the liquid injection tube 15. This tapering brings about acceleration of the gas-liquid mixture during the injection of said mixture, which makes it possible to increase the shear and thus to promote the breakdown of the gas bubbles into gas bubbles of smaller size.

Preferably, the outlet end of the liquid injection tube has tapering of the outlet diameter, as illustrated in FIG. 5B. Said tapering brings about acceleration of the gas-liquid mixture, which makes it possible to increase the shear forces and further improves the breakdown of the gas bubbles into gas bubbles of smaller size.

In a very preferred embodiment, the tube has tapering of the outlet diameter and a deflector.

Preferably, the devices for the injection of gas, preferably gaseous ethylene, and of liquid are positioned in the reaction chamber, preferably in the lower part.

Figure 4:
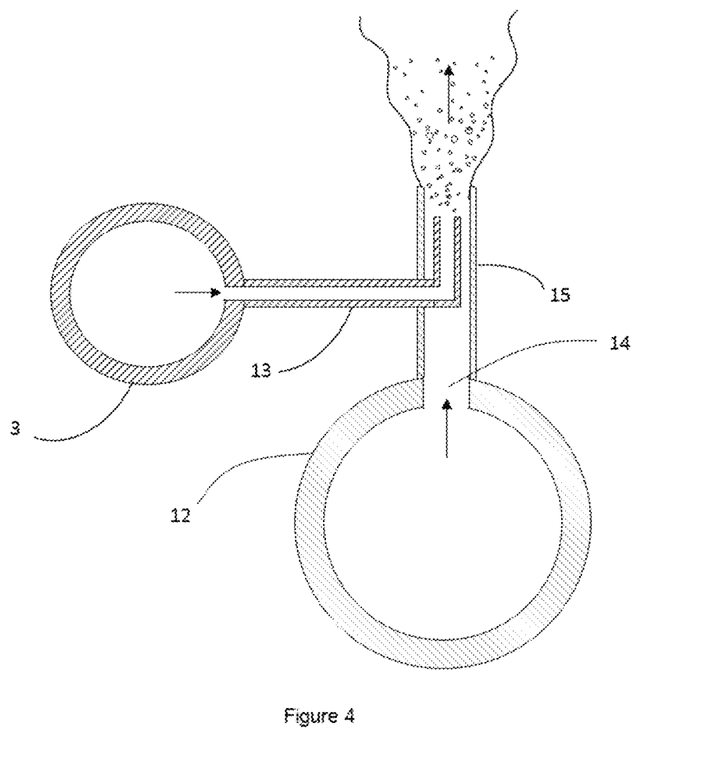
FIG. 4 is a schematic view of a cross section along the vertical axis illustrating a variant of the mode of arrangement of the gas 3 and liquid 12 injection devices. In this variant, the gas injection orifice is extended by a tube 13, and similarly the liquid injection orifice 14 is extended by a tube 15. The gas injection tube 13 has a 90° curvature, and the open end of the tube 13 is positioned concentrically inside the tube 15 extending the injection orifice 14 of the liquid injection device 12. The open end of the gas injection tube 13, at which is found the gas outlet, is positioned at the centre of the liquid injection tube. Thus, the gas and liquid injection streams are oriented in the same direction, and the shear of the gas by the liquid is obtained by the coating and stripping of the gas by the liquid.

Advantageously, a gas injection orifice and a liquid injection orifice are positioned facing each other at an angle of between 0° and 180°. When the orifices of the gas and liquid injection devices are extended by a tube, the gas and liquid injection orifices correspond to the outlet orifices of the gas and liquid injection tube(s). An angle of 0° means that the gas and the liquid are injected via said respective injection orifices on the same trajectory axis and in the same direction, as illustrated in FIG. 4. Preferably, the angle formed by the trajectories is between 0° and 120°, preferably between 30° and 120° and preferably between 45° and 90°. Very preferably, the angle formed by the trajectories is between 0° and 90°. Preferably, the angle formed by the trajectories is equal to 0°, 30°, 45°, 90°, 120° or 180°.

In a particular embodiment, the gas injection device is a cylindrical tube having a circular ring shape, for example round or oval, and having injection orifices. Advantageously, the liquid injection device is also a cylindrical tube having a substantially circular ring shape, for example round or oval, and having injection orifices. In accordance with the invention, said liquid injection device is positioned close to said gas injection device and such that one (or each) gas injection orifice is positioned close to an orifice of the liquid injection device 11 so that the injection trajectory of the liquid is in the same plane as the injection trajectory of the gas so as to bring about the shear of said gas.

Figure 3A:
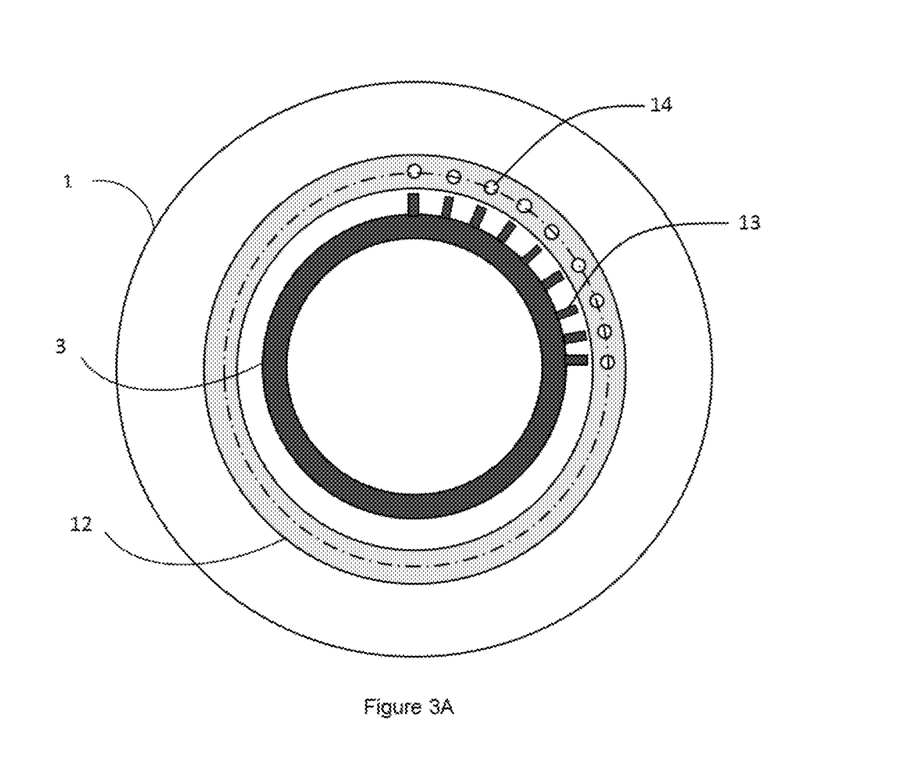
FIG. 3A is a schematic view along the vertical axis of the chamber (which may be above or below) of one embodiment of the gas 3 and liquid 12 injection devices according to the invention arranged in a reaction chamber 1. The gas 3 and liquid 12 injection devices are of circular shape and arranged so that the gas outlet orifices each extended by a tube 13 of the gas injection device 3 inject the gas towards the outer wall of the chamber 1 and the injection trajectory of the gas perpendicularly crosses the trajectory of the liquid injection orifice 14 so as to bring about shear of the gas in order to reduce the bubble size of the injected gas.
Figure 3B:
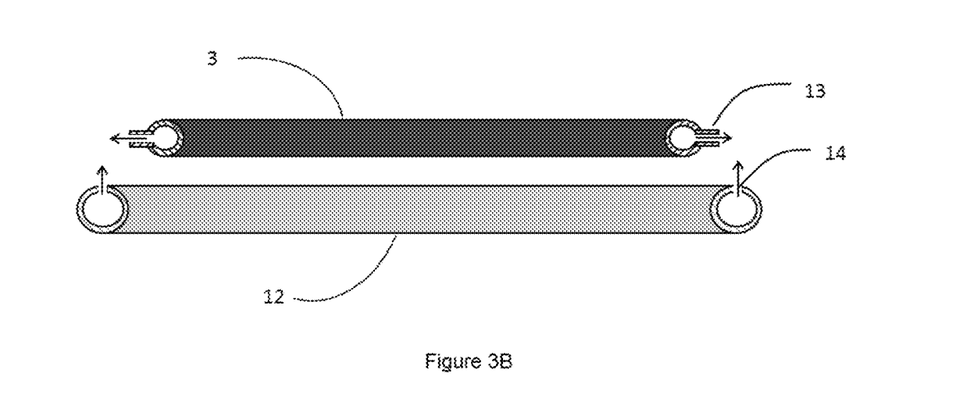
FIG. 3B is a schematic view of a cross section along the vertical axis of the injection device of FIG. 3A. The liquid injection device 12 is a circular ring having a diameter greater than that of the gas injection device 3, which is itself in the form of a circular ring. The liquid injection device 12 is positioned on a different plane from that of the gas injection device 3.
Figure 3C:
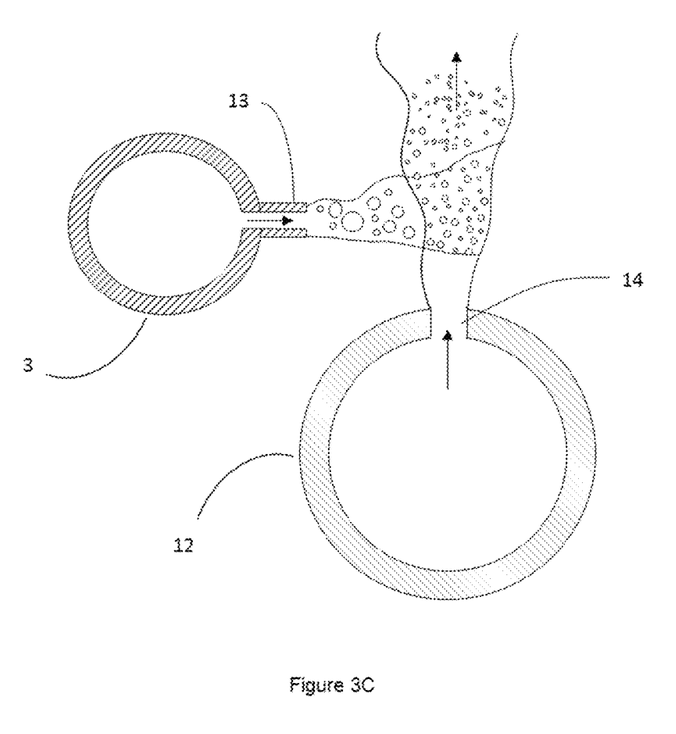
FIG. 3C is a schematic view of a cross section along the vertical axis of the injection devices according to FIG. 3A illustrating the effect of shear of the gas stream injected by the gas injection device 3 by the liquid stream injected by the liquid injection device 12.

Very advantageously, the gas injection device is in ring form, preferably circular, and has a diameter greater or less than that of the liquid injection device in ring form, preferably circular. When the diameter of the gas injection device is less than that of the liquid injection device, the gas injection device is positioned inside the liquid injection device on a different plane, i.e. above or below, as illustrated in FIG. 3A. Conversely, when the diameter of the gas injection device is greater than that of the liquid injection device, the gas injection device is positioned outside the liquid injection device on a different plane, i.e. above or below.

In a particular embodiment, a sequence of several liquid and gas injection devices in the form of a circular ring of decreasing diameters are alternated from the periphery to the centre represented by the central axis of the device having the largest diameter. Said devices are positioned relative to each other so that a gas injection orifice of a gas injection device is positioned close to an orifice of the adjacent liquid injection device so that the injection trajectory of the liquid is in the same plane as the injection trajectory of the gas so as to bring about the shear of said gas.

In particular, the gas/liquid reactor may also comprise:
a reaction chamber 1, of elongated shape along the central vertical axis, which may contain
a liquid phase located in a lower zone, comprising and preferably consisting of the products of the reaction, dissolved and gaseous olefinic feedstock, preferably dissolved and gaseous ethylene, a catalytic system and an optional solvent, and a gas phase, located in an upper zone above the lower zone, comprising gaseous ethylene, and also the uncondensable gases (notably ethane),
  a means for introducing the catalytic system, said means optionally being located in the lower part of the reaction chamber,
  a recirculation loop comprising a withdrawing means at the base (preferably at the bottom) of the reaction chamber for withdrawing a liquid fraction, a heat exchanger for cooling said liquid, and a means for introducing said cooled liquid, said introduction means being located in the upper part of the lower zone of the reaction chamber,
  and optionally a gas phase recycling loop to recycle at least a fraction of the gas phase into the lower zone of the liquid phase, comprising a withdrawing means located in the upper zone of the reaction chamber to enable the withdrawal of a gas fraction in the gas phase and an introduction means positioned in the lower zone of the reaction chamber to enable the introduction of said withdrawn gas fraction into the liquid phase.

Preferably, the reaction chamber 1 is cylindrical. In the case of a cylindrical chamber, the diameter D is the diameter of the cylinder. Such a geometry makes it possible notably to limit the presence of "dead" volumes in the column.

Oligomerization Process

Another subject of the invention relates to the process for the oligomerization of a gaseous olefinic feedstock, preferably gaseous ethylene, using a gas/liquid reactor according to the invention as defined above, said process comprising the contact of a liquid and of the gaseous olefinic feedstock, preferably gaseous ethylene, by means of a gas injection device and a liquid injection device, said injection devices being arranged so that the injection of the liquid brings about a reduction, by shear, of the size of the gaseous ethylene bubbles.

In a fluid in motion, any difference in speed within a fluid brings about shear stresses: the fluid particles that are moving faster are slowed down by those moving less quickly. The contact of a gas phase with a liquid phase which has an injection speed higher than that of the gas brings about shear stresses at the gas/liquid interface, causing breakdown of the gas bubbles. The shear is the result of the turbulence, and may be measured indirectly by measurements of speed fluctuation of each phase or calculated via methods known to those skilled in the art.

Preferably, the injection speed of the liquid is greater than the injection speed of the gaseous olefinic feedstock so as to promote the shear of the gas bubbles and reduction of the size of the olefin gas bubbles to gas bubbles of smaller size.

Preferably, the injection speed of the liquid is between 0.1 and 20 m/s (metres/second) for the liquid, and the injection speed of the gas is between 1.0 and 10 m/s.

The process for the oligomerization of a gaseous olefinic feedstock using the reactor according to the invention makes it possible to produce linear α-olefins by placing in contact said olefinic feedstock and a catalytic system, optionally in the presence of a solvent.

The gaseous olefinic feedstock preferably comprises between 2 and 6 carbon atoms, preferably between 2 and 4 carbon atoms. Preferably, the olefinic feedstock is chosen from butene, more particularly isobutene or 1-butene, propylene and ethylene, alone or as a mixture.

All the catalytic systems known to those skilled in the art and capable of being employed in dimerization, trimerization or tetramerization processes and more generally in the oligomerization processes according to the invention come within the field of the invention. Said catalytic systems and their implementation are notably described in patent applications FR 2 984 311, FR 2 552 079, FR 3 019 064, FR 3 023 183, FR 3 042 989 or also in patent application FR 3 045 414.

Preferably, the catalytic systems comprise, and preferably consist of:
  a metal precursor, preferably based on nickel, titanium or chromium,
  optionally an activating agent,
  optionally an additive, and
  optionally a solvent.

The Metal Precursor

The metal precursor used in the catalytic system is chosen from compounds based on nickel, titanium or chromium.

In one embodiment, the metal precursor is based on nickel and preferentially comprises nickel in (+II) oxidation state. Preferably, the nickel precursor is chosen from nickel(II) carboxylates, for instance nickel 2-ethylhexanoate, nickel (II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula [Ti(OR)$_4$] in which R is a linear or branched alkyl radical. Among the preferred alkoxy radicals, non-limiting examples that may be mentioned include tetraethoxy, tetraisopropoxy, tetra(n-butoxy) and tetra(2-ethylhexyloxy).

The titanium aryloxy compound advantageously corresponds to the general formula [Ti(OR')$_4$] in which R' is an aryl radical which is unsubstituted or substituted with alkyl or aryl groups. The radical R' may include heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy, the biphenoxy radical, binaphthoxy and 1,8-naphthalenedioxy.

According to a third embodiment, the metal precursor is based on chromium and preferentially comprises a chromium(II) salt, a chromium(III) salt or a salt of different oxidation state which may include one or more identical or different anions, for instance halides, carboxylates, acetylacetonates or alkoxy or aryloxy anions. Preferably, the chromium-based precursor is chosen from CrCl$_3$, CrCl$_3$(tetrahydrofuran)$_3$, Cr(acetylacetonate)$_3$, Cr(naphthenate)$_3$, Cr(2-ethylhexanoate)$_3$ and Cr(acetate)$_3$.

The concentration of nickel, titanium or chromium is between 0.001 and 300.0 ppm by mass of atomic metal, relative to the reaction mass, preferably between 0.002 and 100.0 ppm, preferentially between 0.003 and 50.0 ppm, more preferentially between 0.05 and 20.0 ppm and even more preferentially between 0.1 and 10.0 ppm by mass of atomic metal, relative to the reaction mass.

The Activating Agent

Optionally, irrespective of the metal precursor, the catalytic system comprises one or more activating agents chosen from aluminium-based compounds, such as methylaluminium dichloride (MeAlCl$_2$), dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$), diethylethoxyaluminium (Et$_2$AlOEt), methylaluminoxane (MAO), ethylaluminoxanes (MMAO) and modified methylaluminoxanes (MMAO).

The Additive

Optionally, the catalytic system comprises one or more additives.

The additive is chosen from monodentate phosphorus-based compounds, bidentate phosphorus-based compounds, tridentate phosphorus-based compounds, olefinic compounds, aromatic compounds, nitrogenous compounds, bipyridines, diimines, monodentate ethers, bidentate ethers, monodentate thioethers, bidentate thioethers, monodentate or bidentate carbenes, mixed ligands such as phosphinopyridines, iminopyridines, bis(imino)pyridines.

When the catalytic system is based on nickel, the additive is chosen from:
compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or compounds corresponding to the general formula (I) or one of the tautomers of said compound:

(I)

in which:
A and A', which may be identical or different, are independently an oxygen or a single bond between the phosphorus atom and a carbon atom, the groups R$^{1a}$ and R$^{1b}$ are independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-bis(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups, the group R$^2$ is independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-bis (2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the catalytic system is based on chromium, the additive is chosen from:

compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or aryloxy compounds of general formula $[M(R^3O)_{2-n}X_n]_y$, in which:

M is chosen from magnesium, calcium, strontium and barium, preferably magnesium, $R^3$ is an aryl radical containing from 6 to 30 carbon atoms and X is a halogen or an alkyl radical containing from 1 to 20 carbon atoms, n is an integer which can take the values of 0 or 1, and y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals may be borne by the same molecule, for instance the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

The Solvent

In another embodiment according to the invention, the catalytic system optionally comprises one or more solvents.

In one embodiment, a solvent or a mixture of solvents may be used during the oligomerization reaction.

The solvent(s) are advantageously chosen from ethers, alcohols, halogenated solvents and hydrocarbons, which may be saturated or unsaturated, cyclic or non-cyclic, aromatic or non-aromatic, comprising between 1 and 20 carbon atoms, preferably between 4 and 15 carbon atoms, preferentially between 4 and 12 carbon atoms and even more preferentially between 4 and 8 carbon atoms.

Preferably, the solvent is chosen from pentane, hexane, cyclohexane, methylcyclohexane, heptane, butane or isobutane, 1,5-cyclooctadiene, benzene, toluene, ortho-xylene, mesitylene, ethylbenzene, diethyl ether, tetrahydrofuran, 1,4-dioxane, dichloromethane, dichloroethane, tetrachloroethane, hexachloroethane, chlorobenzene, dichlorobenzene, butene, hexene and octene, pure or as a mixture.

Preferably, the solvent may be advantageously chosen from the products of the oligomerization reaction. Preferably, the solvent used is cyclohexane.

Preferably, when a solvent is used in the oligomerization process, the mass content of solvent introduced into the reactor used in the process according to the invention is between 0.2 and 10.0, preferably between 0.5 and 5.0, and in a preferred manner between 1.0 and 4.0. The content of solvent is the mass ratio of the total flow rate of injected solvent to the total flow rate of injected gaseous ethylene in the process.

Preferably, the linear α-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear α-olefins chosen from 1-butene, 1-hexene and 1-octene.

Advantageously, the oligomerization process is performed at a pressure of between 0.1 and 10.0 MPa, preferably between 0.2 and 9.0 MPa and preferentially between 0.3 and 8.0 MPa, at a temperature of between 30 and 200° C., preferably between 35 and 150° C. and in a preferred manner between 45 and 140° C.

Preferably, the concentration of catalyst in the catalytic system is between 0.001 and 300.0 ppm by mass of atomic metal relative to the reaction mass, preferably between 0.002 and 100.0 ppm, preferentially between 0.003 and 50.0 ppm, more preferentially between 0.05 and 20.0 ppm and even more preferentially between 0.1 and 10.0 ppm by mass of atomic metal relative to the reaction mass.

According to one embodiment, the oligomerization process is performed batchwise. The catalytic system, constituted as described above, is introduced into a reactor according to the invention, advantageously equipped with heating and cooling devices, then pressurization with ethylene is performed to the desired pressure, and the temperature is adjusted to the desired value. The pressure in the reactor is kept constant by introduction of the gaseous olefinic feedstock until the total volume of liquid produced represents, for example, from 1 to 1000 times the volume of the catalytic solution introduced beforehand. The catalyst is then destroyed by any usual means known to a person skilled in the art and the reaction products and the solvent are then withdrawn and separated.

According to another embodiment, the oligomerization process is performed continuously. The catalytic system, constituted as described above, is injected at the same time as the gaseous olefinic feedstock, preferably ethylene, into the reactor according to the invention, and maintained at the desired temperature. The components of the catalytic system can also be injected separately into the reaction medium. The gaseous olefinic feedstock, preferably gaseous ethylene, is introduced via an inlet valve controlled by the pressure, which keeps the latter constant in the reactor. The reaction mixture is withdrawn by means of a liquid-level-control valve, so as to keep said level constant. The catalyst is destroyed continuously by any usual means known to a person skilled in the art and the products resulting from the reaction, and also the solvent, are then separated out, for example by distillation. The ethylene which has not been converted can be recycled into the reactor. The catalyst residues included in a heavy fraction can be incinerated.

EXAMPLES

The examples below illustrate the invention without limiting the scope thereof.

Example 1 (Comparative)

The ethylene oligomerization process is performed in a bubble column reactor. The reactor is operated at a pressure of 5.0 MPa and at a temperature of 120° C. The reaction volume is composed, in accordance with FIG. 1, of two zones A and B, a column with a diameter of 2.97 m and a liquid height of 6.0 m, and a recirculation loop having a total volume of 5.0 m$^3$.

The column is equipped with a device for injecting gaseous ethylene, located 1.0 m from the bottom of the column.

The catalytic system introduced into the reaction chamber is a chromium-based catalytic system having a chromium content of 5.2 ppm, as described in patent FR 3 019 064, in the presence of cyclohexane as solvent.

The purge flow rate is 0.0045 kg/s.

The volumetric productivity of this reactor is 0.13 tonne of 1-hexene produced per hour per m$^3$ of reaction volume.

The performance levels of this reactor enable a saturation with dissolved ethylene of 52.6%.

The production of 1-hexene is 6.25 tonnes/hour, the selectivity for 1-hexene is 80.5 wt %, and the residence time in the reactor is 78.5 minutes, for a mass proportion of solvent of 1.0. Said mass proportion of solvent is calculated as the mass ratio of the flow rate of injected solvent to the flow rate of injected gaseous ethylene.

Example 2 (According to the Invention)

Figure 2:
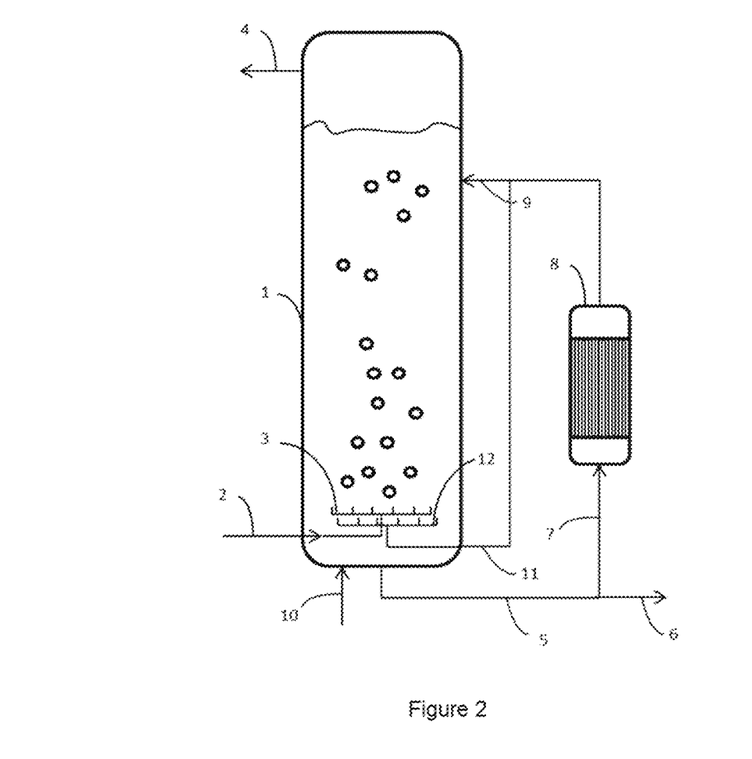

The ethylene oligomerization process is performed in a bubble-column type gas/liquid reactor. The reactor is operated at a pressure of 5.0 MPa and at a temperature of 120° C. The reaction volume is composed, in accordance with FIG. 2, of two zones A and B, a column with a diameter of 2.97 m and a liquid height of 6.0 m, and a recirculation loop having a total volume of 5.0 m$^3$.

The column is equipped, according to the invention, with a gaseous ethylene injection device and a liquid product injection device, which makes it possible to reduce the initial size of the ethylene bubbles by a factor of 5. These distributors are located 1.0 m from the bottom of the column.

The catalytic system introduced into the reaction chamber is a chromium-based catalytic system having a chromium content of 3.0 ppm, as described in patent FR 3 019 064, in the presence of cyclohexane as solvent.

The purge flow rate is 0.0045 kg/s.

The volumetric productivity of this reactor is the same as in the preceding example.

The performance levels of this reactor enable a saturation with dissolved ethylene of 90.5%.

The production of 1-hexene is 6.25 tonnes/hour, the selectivity for 1-hexene is 83.3 wt %, and the residence time in the reactor is 69.8 minutes, for a mass proportion of solvent of 1.0. Said proportion of solvent is calculated as the mass ratio of the flow rate of injected solvent to the flow rate of injected gaseous ethylene.

The device according to the invention thus makes it possible to improve the saturation with ethylene by 37.9%, and thus the selectivity for α-olefin by 2.8% while reducing the consumption of catalyst (72% on the catalytic concentration) and thus the operating cost of the process, relative to the case according to the prior art.

The invention claimed is:

1. A process for the oligomerization of a gaseous olefinic feedstock, comprising:
the contact of a liquid comprising a catalytic system comprising a metal catalyst, at least one activator and at least one additive, and optionally a solvent; and the gaseous olefinic feedstock by a gas injection device and a liquid injection device, said injection devices being arranged so that the injection of the liquid brings about a reduction, by shear, in the size of the gaseous olefinic feedstock bubbles, said process using a gas/liquid reactor for the oligomerization of the gaseous olefinic feedstock comprising a gas injection device (3) comprising at least one gas injection orifice and a liquid injection device (12) comprising at least one liquid injection orifice, each gas injection orifice being located close to an orifice of the liquid injection device (11) and positioned so that the injection trajectory of the gas is in the plane of the injection trajectory of the liquid.

2. The process according to claim 1, in which the at least one liquid injection orifice and the at least one gas injection orifice are circular, and in which the at least one liquid injection orifice have a diameter greater than or equal to the diameter of the at least one gas injection orifice.

3. The process according to claim 1, in which at least one gas injection orifice and at least one liquid injection orifice are positioned facing each other at an angle of between 0° and 180°.

4. The process according to claim 1, in which the gas injection and liquid injection devices are chosen from a pipe, a network of pipes, a multitubular distributor, a perforated plate, a cylindrical tube or a concentric tube.

5. The process according to claim 1, in which the gas injection device is a cylindrical tube in the form of a circular ring having injection orifices and the liquid injection device is a cylindrical tube in the form of a circular ring having injection orifices.

6. The process according to claim 1, in which the gas injection device in the form of a circular ring has a diameter less than that of the liquid injection device in the form of a circular ring, and in which said gas injection device is positioned inside the liquid injection device on a different plane.

7. The process according to claim 1, in which a sequence of several liquid and gas injection devices in the form of a circular ring of decreasing diameters are alternated from the periphery to the centre represented by the central axis of the device having the largest diameter, said devices being positioned so that a gas injection orifice of a gas injection device is positioned close to an orifice of the adjacent liquid injection device so that the injection trajectory of the liquid is in the same plane as the injection trajectory of the gas so as to bring about shear of said gas.

8. The process according to claim 1, in which the orifices of the gas and liquid injection devices are each extended by a tube (13, 15).

9. The process according to claim 8, in which the tube(s) (13) of the gas injection device (3) have a diameter smaller than that of the tube(s) (15) of the liquid injection device (12) and an open outlet end of the tube (13) of the gas injection device (3) is positioned coaxially inside the liquid injection tube.

10. The process according to claim 8, in which the liquid injection tube (15) comprises a deflector.

11. The process according to claim 8, in which the end of the liquid injection tube (15) has tapering of the outlet diameter.

12. The oligomerization process according to claim 1, in which the gaseous olefinic feedstock comprises between 2 and 6 carbon atoms.

13. The oligomerization process according to claim 1, in which the injection speed of the liquid is greater than the injection speed of the gaseous olefinic feedstock so as to promote shear of the size of the olefin gas bubbles to gas bubbles of smaller size.

14. The oligomerization process according to claim 1, in which the gaseous olefinic feedstock comprises between 2 and 4 carbon atoms.

15. The process according to claim 1, comprising:
a reaction chamber, of elongated shape along a vertical axis, which may contain a liquid phase located in a lower zone, comprising the products of the reaction, dissolved and gaseous olefinic feedstock, a catalytic system and an optional solvent, and a gas phase, located in an upper zone above the lower zone, comprising gaseous olefinic feedstock, and also uncondensable gases,
a pipe for introducing the catalytic system, said pipe being located in the lower part of the reaction chamber,
a recirculation loop comprising a withdrawing pipe at the base of the reaction chamber for withdrawing a liquid fraction, a heat exchanger for cooling said liquid, and a pipe for introducing said cooled liquid, the introduction pipe being located in the upper part of the lower zone of the reaction chamber,
and optionally a gas phase recycling loop to recycle at least a fraction of the gas phase into the lower zone of the liquid phase, comprising a withdrawing pipe located in the upper zone of the reaction chamber to enable the withdrawal of a gas fraction in the gas phase and an introduction pipe positioned in the lower zone of the reaction chamber to enable the introduction of said withdrawn gas fraction into the liquid phase.

16. The process according to claim 15, wherein the liquid phase located in the lower zone consists of the products of the reaction, dissolved and gaseous olefinic feedstock, a catalytic system and an optional solvent.

17. The process according to claim 15, wherein, in the liquid phase located in a lower zone, the dissolved and gaseous olefinic feedstock is dissolved and gaseous ethylene.

18. The process according to claim 15, wherein, in the gas phase, located in an upper zone above the lower zone, the gaseous olefinic feedstock is gaseous ethylene.

19. The process according to claim 15, wherein the uncondensable gases include ethane.

* * * * *